United States Patent [19]

Rutzen et al.

[11] 4,339,616

[45] Jul. 13, 1982

[54] PROCESS FOR THE MANUFACTURE OF 1,2-DIOLS HAVING AT LEAST 4 CARBON ATOMS

[75] Inventors: Horst Rutzen, Langenfeld; Wolfgang Rupilius, Düseldorf-Urdenbach, both of Fed. Rep. of Germany

[73] Assignees: Henkel Kommanditgesellschaft auf Aktien, Düsseldorf-Holthausen; Deutsche Gold-und Silberscheide Anstalt Vormals Roessler, Frankfurt am Main, both of Fed. Rep. of Germany

[21] Appl. No.: 187,530

[22] Filed: Sep. 15, 1980

[30] Foreign Application Priority Data

Sep. 21, 1979 [DE] Fed. Rep. of Germany ....... 2938154

[51] Int. Cl.$^3$ .............................................. C07C 29/10
[52] U.S. Cl. ................................................... 568/867
[58] Field of Search ....................................... 568/867

[56] References Cited

U.S. PATENT DOCUMENTS 2,807,651  9/1957  Britton et al. ...................... 568/867
3,808,280  4/1974  Merger et al. ...................... 568/853
3,933,923  1/1976  Osberghaus et al. ............... 568/680

FOREIGN PATENT DOCUMENTS 1177877  1/1970  United Kingdom ................ 568/867
1338196  11/1973  United Kingdom .

*Primary Examiner*—Natalie Trousof
*Assistant Examiner*—Frederick W. Pepper
*Attorney, Agent, or Firm*—Hammond & Littell, Weissenberger and Muserlian

[57] ABSTRACT

A process for the preparation of 1,2-diols having at least 4 carbon atoms by hydrolysis of the corresponding 1,2-epoxide compound with water in the presence of catalysts at elevated temperatures characterized in that salts of primary, secondary and/or tertiary amines with organic and/or inorganic acids, and/or quaternary ammonium salts, are used as catalysts.

12 Claims, No Drawings

PROCESS FOR THE MANUFACTURE OF 1,2-DIOLS HAVING AT LEAST 4 CARBON ATOMS

BACKGROUND OF THE INVENTION

The preparation of 1,2-diols with a larger number of carbon atoms is a technically not yet satisfactorily solved problem. The preparation by hydrolysis of the corresponding 1,2-epoxide compound has been recommended repeatedly, but no solution satisfactory in all respects has yet been found. Disadvantages of the processes known so far are particularly the high consumption of chemicals and/or the high temperatures and the high pressures associated with this, which are required for the production of satisfactory yields.

For example, a process starting with the corresponding olefins and proceeding via the formation of epoxides is suggested by Swern et al in J. Am. Chem. Soc. 68: 1504–1507, 1946. Here, a large excess of formic acid is required as solvent and oxygen transfer agent (performic acid). The consumption of chemicals is increased, in addition, by the fact that the diol esters formed first are saponified with alcoholic potassium hydroxide solution.

The process of Merk et al, German published application De-OS No. 22 03 806, which utilizes a 2% sodium hydroxide solution for the epoxide hydrolysis, requires a smaller amount of chemicals. Here the disadvantages are the high reaction temperature (250° C.) and the high pressure (about 40 atm.) which make complex pressure equipment necessary. The exchange of the sodium hydroxide solution for di- and monocarboxylic acid salts improves the diol yields, but requires the same high reaction temperatures.

The suggestion is made by Osberghaus et al U.S. Pat. No. 3,933,923, to achieve a greater yield by the use of acetone as solubilizer and disodium azelate as hydrolyzing agent. The work must be carried out at high temperature (250° C.) and corresponding pressures, even in this case. It is also known that acid hydrolysis with dilute sulfuric acid produces considerable quantities of epoxide polymers in addition to about 50% diol.

For the hydrolysis of short-chain epoxides (ethylene oxide and propylene oxide), Cipriani et al, German Published Application DE-OS No. 26 15 595, recommend working in the presence of tertiary amines (triethylamine) and carbon dioxide at 110° C. and 19 bar, with a hydrolysis time of 2 hours. The short-chain glycol forms with high selectivity. The application of this reaction to epoxide compounds with a larger number of carbons has failed so far.

OBJECTS OF THE INVENTION

An object of the present invention is to develop a process for the preparation of 1,2-diols having at least 4 carbon atoms while avoiding as much as possible the disadvantages and restrictions of the presently known processes for the hydrolysis of 1,2-epoxide compounds with at least 4 carbon atoms.

Another object of the present invention is the development of a process for the preparation of 1,2-diols having at least 4 carbon atoms by hydrolysis of the corresponding 1,2-epoxide compound with water in the presence of catalysts at elevated temperatures characterized in that salts of primary, secondary and/or tertiary amines with organic and/or inorganic acids, and/or quaternary ammonium salts, are used as catalysts.

A further object of the present invention is to develop an improvement in the process for the production of 1,2-diols having at least 4 carbon atoms comprising subjecting a 1,2-epoxide having at least 4 carbon atoms to hydrolysis with water in the presence of a catalyst at elevated temperatures and recovering 1,2-diols having at least 4 carbon atoms, the improvement consisting of employing a catalyst system selected from the group consisting of (1) salts of primary amines, secondary amines and/or tertiary amines with organic and/or inorganic acids, (2) quaternary ammonium salts, and (3) mixtures thereof, as said catalyst.

These and other objects of the invention will become more apparent as the description thereof proceeds.

DESCRIPTION OF THE INVENTION

We have now discovered an improvement in the existing process whereby the preparation of the corresponding 1,2-diols with at least 4 carbon atoms at the lowest possible temperatures and low pressures within economically feasible reaction times is to be made accessible. The invention has as its particular task the further development of the hydrolytic cleavage of 1,2-epoxide compounds, which is well-known as such, by the selection and application of a new catalyst system, to approach an optimal compromise between reaction conditions and yield.

The present invention relates to a process for the preparation of 1,2-diols with a higher number of carbon atoms by cleaving the corresponding 1,2-epoxide compounds with water in the presence of catalysts at elevated temperatures. The process according to the invention is characterized by work with catalysts, or catalyst systems which contain salts of primary, secondary and/or tertiary amines with organic and/or inorganic acids. In addition to or instead of these catalyst components, quaternary ammonium salts with inorganic or organic acid radicals may be used according to the invention to accelerate and steer the epoxide hydrolysis.

More particularly, the present invention is directed toward an improvement in the process for the preparation of higher 1,2-diols and/or higher 1,2-polyols which comprises hydrolyzing the corresponding epoxides of the formula

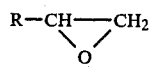

in which R is selected from the group consisting of alkyl having 2 to 28 carbon atoms, haloalkyl having 2 to 28 carbon atoms, alkoxyalkyl having 2 to 28 carbon atoms, epoxyalkyl having 3 to 28 carbon atoms, haloepoxyalkyl having 3 to 28 carbon atoms, alkoxyepoxyalkyl having from 4 to 28 carbon atoms, and mixtures thereof, with the proviso that the total number of carbon atoms in the epoxide is from 4 to 30 carbon atoms, with a solution of a catalyst, and recovering said diols and/or polyols; the improvement consisting of employing a catalyst system selected from the group consisting of (1) salts of primary amines, secondary amines and/or tertiary amines with organic and/or inorganic acids, (2) quaternary ammonium salts, and (3) mixtures thereof, as said catalyst.

The work according to the invention is carried out preferably with catalyst systems based on salts of the primary, secondary and/or tertiary amines with monocarboxylic or polycarboxylic acids.

Especially suitable as epoxide compounds with a higher number of carbon atoms are respective starting materials that contain from 4 to 30 carbon atoms, among which the compounds with about 6 to 20 carbon atoms have special technical significance. The process according to the invention is suitable for the conversion of respective aliphatic epoxides, but also equally well for the conversion of aromatic epoxides, provided that the employed epoxide compounds contain at least one terminal epoxide group, the 1,2-epoxide grouping. The process according to the invention is particularly applicable also to such epoxide compounds with more than only one terminal epoxide grouping.

Epoxide compounds of the mentioned type are derived, for example, from the respective α-olefins or araliphatic compounds that are unsaturated in the terminal position. However, also especially suitable as starting materials for the purposes of the invention are corresponding oxa-compounds, i.e., structurally analogous compounds in which one part of the molecule containing the 1,2-epoxy group is bound to the higher molecular-weight hydrocarbon radical through an oxygen atom. Particularly easily accessible in this case are the respective glycide ethers, and again the starting material may have bound to it one or several of the glycide groupings.

The starting materials particularly suitable for the process according to the invention can be summarized under the general formula

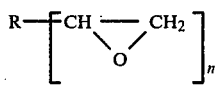

wherein R represents a radical having from 2 to 28 carbon atoms which can be open-chained or cyclic, saturated or unsaturated, such as alkyl, alkenyl, alkadienyl, cycloalkyl, cycloalkenyl or also aromatic, such as phenyl or naphthyl. Preferably the number of carbon atoms in R is from 4 to 18, and most particularly from 8 to 18. Instead of the pure hydrocarbon radicals, comparable radicals with hetero-atoms, for example oxa-atoms, may be present. In the given general formula, n stands preferably for a whole number that can be equal to or greater than 1, and up to 5, preferably 1 to 3. Particularly important may be compounds in which n has the value of 1, and of those again such in which R is an aliphatic, saturated hydrocarbon radical (alkyl) with 8 to 18 carbon atoms.

When the epoxide compounds can be derived from terminal olefins, the 1,2-epoxy group usually is bound exclusively by means of carbon bonds to the radical R. In the above-described case of the corresponding oxa-compounds, an -0- bridge is provided as connecting member between the molecular component carrying the epoxide ring and the rest of the molecule. In the case of the glycide compounds especially preferred according to the invention, the radical R from the previously given general formula then has the meaning

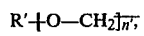

in which R' has the meaning of R and n' is the same as n. The process according to the invention is particularly suitable for the hydrolytic cleavage of 1,2-epoxide compounds, which are miscible with water to a limited degree only, due to their higher number of carbon atoms or their molecular structure. The use of the new catalyst systems described below permits an effective hydrolytic cleavage under comparably moderate process conditions especially for this class of substances and makes an optimal improvement in the yield of product under these conditions possible.

Suitable examples of the epoxides to be hydrolyzed according to the process of the invention include: epoxyalkanes having 4 to 30 carbon atoms, preferably 4 to 20 carbon atoms, for example, 1,2-epoxybutane, 1,2-epoxyhexane, 1,2-epoxyoctane, 1,2-epoxydodecane, 1,2-epoxytetradecane, 1,2-epoxyhexadecane, 1,2-epoxyoctadecane, 1,2-epoxyheptadecane; and diepoxyalkanes having 4 to 30 carbon atoms, preferably 8 to 20 carbon atoms, such as 1,2,7,8-diepoxyoctane, as well as epoxy (alkyl) oxaalkanes having 4 to 30 carbon atoms such as cetyl glycidyl ether, phenyl epoxides such as styrene oxide and epoxyalkoxy substituted aromatic compounds such as bisphenol-A diglycidyl ether.

The catalysts or catalyst systems preferred according to the invention are built of primary, secondary and/or tertiary amines as one component, and salt-forming inorganic or organic acids as the other component. The preferred acids are monocarboxylic or polycarboxylic acids.

The base component and the acid component are used advantageously in stoichiometrically approximately equal amounts. In a preferred form of execution, however, an excess of the acid component beyond the amount required for the formation of the salt is used. Even a slight excess of acid component in the catalyst system can result in a considerable acceleration of the reaction and an improved yield, under standard conditions. The acid component can be used in an amount several times, for example two to three times, that stoichiometrically required for the formation of the salt with the base component. In general, however, the desired acceleration of the reaction is achieved with catalyst systems alone, which contain the acid component in amounts of up to twice that required stoichiometrically for the formation of the salt. Particularly preferred can be the working with stoichiometric ratios of base to acid in the range from 1:1.1 to 1.8, especially 1:1.1 to 1.5.

This catalyst system is added to the reaction mixture in limited amounts. Suitable are, for example, amounts of 0.5 to 10 mol %, particularly 1 to 6 mol % of the amine salt catalyst system, based on the amount of epoxide charged.

An acceleration of the reaction principally is obtained with any primary, secondary and/or tertiary amine as the base component of the catalyst system. However, for the optimal improvement of the procedural results, a selection of the basic amine components to be used is advantageous. This selection is determined, in a preferred form of execution, by the carbon number of the amines and their adaptation to the carbon number of the epoxide compounds to be converted. The following criteria of selection apply to the three classes of primary, secondary and tertiary amines:

Primary Amines: The sum of the carbon atoms of the primary amine + three times the sum of the carbon atoms of the epoxide compound to be converted advantageously amounts to 13 to 40. Especially preferred, this sum of carbon atoms lies in the range from 12 to 30.

Secondary Amines: Here the sum of the carbon atoms of the secondary amine + twice the carbon atoms of the epoxide to be converted also amounts to 10 to 40.

Again, the numerical value of this sum of carbon atoms lies in the range from 12 to 30 in the particularly preferred form of execution.

Tertiary Amines: Accordingly it applies for this class of compounds that the sum of the carbon atoms of the tertiary amine + the sum of the carbon atoms of the epoxide again lies in the range from 7 to 40, the preferred numerical value again being 12 to 30.

This selection of the amines seems to favor especially a distribution of the catalyst system in the heterogeneous reaction mixture, under the reaction conditions, thus providing a change for the optimal improvement of the results of the process. Here the amines appear to undergo an alkylation and quaternization by conversion with the epoxides, under the influence of the acid catalyst component.

Preferred amines of the mentioned type are aliphatic, cycloaliphatic and araliphatic amines. Aromatic amines also may be used, however. The use of short-chain amines can lead to particularly favorable results. Short-chain aliphatic amines, such as monoalkyl amines, dialkylamines and trialkylamines having from 1 to 8 carbon atoms in each alkyl, and here especially secondary amines of this type, can produce especially advantageous results. Dialkylamines with up to 8 carbon atoms, preferably with up to 4 carbon atoms, are a preferred basic component for the catalyst systems used according to the invention. A typical example is dimethylamine. Other important amines are described in the following examples. The amines can be unsubstituted or substituted and unsubstituted amines are generally preferred. When substituents are present, the basicity of the amines should not be impaired too strongly by them. Suitable substituents are, for example, hydroxyl groups, provided that they are not present on the amine in an excessive accumulation. Among the amines are monoalkyl amines having from 1 to 18 carbon atoms, dialkyl amines having from 1 to 18 carbon atoms in each alkyl, trialkylamines having from 1 to 18 carbon atoms in each alkyl, alkylol-dialkyl amines having from 1 to 18 carbon atoms in each alkyl and alkylol, phenylalkylamines having from 1 to 8 carbon atoms in the alkyl, cyclodiazaalkanes having 4 to 8 carbon atoms, pyridinyl-dialkyl amine having from 1 to 8 carbon atoms in the alkyl, etc.

The monocarboxylic and/or polycarboxylic acids used preferably according to the invention for the formation of salt have from 1 to 26 carbon atoms. Suitable are principally organic acids from the aliphatic, the aromatic and the heterocyclic series, and these acids may be substituted or unsubstituted and saturated or mono- or polyunsaturated.

Typical examples for carboxylic acids of the mentioned type are aliphatic monocarboxylic acids of the mentioned carbon number range, especially those with 2 to 18, preferably 2 to 14, carbon atoms, which also are olefinically unsaturated, if desired, for example, alkanoic acids having 1 to 26 carbon atoms, preferably 2 to 14 carbon atoms, such as acetic acid, propionic acid, butyric acid, capronic acid, caprylic acid, pelargonic acid, lauric acid, myristic acid, palmitic acid, stearic acid, and arachic acid, and, for example, alkenoic acids having 3 to 26 carbon atoms, preferably 3 to 14 carbon atoms, such as acrylic acid, methacrylic acid and allylacetic acid, lauroleic acid, myristoleic acid, palmitoleic acid, oleic acid, gadoleic acid and erucic acid. Other suitable examples include linear or branched aliphatic polycarboxylic acids having 2 to 26 carbon atoms, preferably 2 to 14 carbon atoms, for example, alkanedioic acids having 2 to 26 carbon atoms, preferably 2 to 14 carbon atoms, such as oxalic acid, malonic acid, succinic acid, adipic acid, azelaic acid and sebacic acid, and, for example, alkenedioic acids having 4 to 26 carbon atoms, preferably 4 to 14 carbon atoms, such as maleic acid and fumaric acid, and for example, alkanetrioic acids and hydroxy-alkanetrioic acids having from 4 to 26 carbon atoms, preferably 6 to 14 carbon atoms, such as citric acid. Examples of substituted carboxylic acids having from 2 to 26, preferably 2 to 14, carbon atoms, are hydroxyalkanoic acids, chloroalkanoic acids, dichloroalkanoic acids, trichloroalkanoic acids. Suitable aromatic carboxylic acids are, for example, benzoic acid, phenylalkanoic acids having from 8 to 24 carbon atoms, or phenylalkenoic acids having from 9 to 24 carbon atoms such as cinnamic acid, substituted aromatic carboxylic acids, for example, aminobenzoic acids; as well as the benzene dicarboxylic acids of the type of phthalic acid, isophthalic acid or terephthalic acid. Suitable are further heterocyclic carboxylic acids such as pyromucic acid, tetrahydrofuran carboxylic acids and similar compounds.

The selection of the acid in the catalyst system provides another opportunity for the monitoring of the improvement of the result of the process. Short-chain acids, for example acetic acid, boost the water solubility of the catalyst system, acids with longer chains increase its oleophilic character.

Inorganic acids are also suitable as the acid catalyst component, however. In particular, strong mineral acids, such as phosphoric acid and its partial salts, amidosulfonic acid, nitric acid, hydrochloric acid and sulfuric acid.

Improvements suitable for technical process could be obtained, for example, with catalyst systems based on dimethylamine/acetic acid or dimethylamine/lauric acid. The examples again show additional, especially suitable combinations.

When preformed quaternary ammonium salts are added as catalysts to the reaction mixture, these also have distinct, catalytic effect. Tetraalkyl ammonium salts or phenylalkyl trialkyl ammonium salts may be mentioned as examples. The acid radical in these quaternary salts can be inorganic or organic in nature. Suitable are, for example, the quaternary ammonium halide salts, but acids of the above-mentioned type can represent the acid radical of the quaternary salt equally well. Since, as described above, the amine salts also are presumably converted into quaternary salts by reaction with the epoxides, under the reaction conditions, the suitability of the quaternary ammonium salts as catalysts for the process according to the invention appears logical. Suitable catalysts of this type are, for example, methyltrioctyl ammonium chloride, quaternary salts containing, at the ammonium nitrogen, two long-chain and two short-chain aliphatic alkyl radicals or one long-chain and two short-chain aliphatic alkyl radicals as well as a phenylalkyl radical. Also suitable are quaternary products derived from hydroxyamines.

When such quaternary salts are used as catalysts, the use in the process of limited amounts of acid component in addition to the separately preformed quaternary salt may be preferred according to the invention. The statements made earlier regarding the extent of the acid excess beyond the amount of acid required for the formation of salt with the basic amine component apply here. All previously mentioned inorganic and particularly organic acids can be used as acid components.

There exists principally no upper limit with respect to the amount of water to be used together with the epoxide. However, the fact that the work can be performed with the additon of only a small excess of water while producing high yields of the desired product of the process, is an important advantage of the process according to the invention. As a rule, the amount of water does not exceed 10 mols of water per mol of epoxide. However, the desired conversions can be achieved even with amounts of up to 5 mols of water per mol of epoxide. The minimum amount of water corresponds to the theoretical requirement of 1 mol per mol of epoxide. Usually the reaction is carried out with amounts of 1 to 3 mols of water per mol of epoxide. This possibility of limiting the amount of water has a good effect on the economy of the process.

The reaction temperature usually lies at least at 100° C. Particularly suitable is the range from 100° to 180° C. It may be desirable not to exceed 160° C. as the upper reaction temperature. Satisfactory yields of 1,2-diols can be obtained within acceptable periods of time, even at temperatures as low as 120° C. or 100° C. by adjusting the process variables and especially by selecting the suitable catalyst systems. The range from 100° to 150° C. may be considered as an especially important temperature range.

The process pressures depend on the chosen process temperature. Working without pressure, at the boiling point of water, is possible with the suitable selection of highly active catalyst systems. Other catalyst systems require higher temperatures and thus elevated pressures. The suitable pressure range usually lies between 1 and 10 bar, preferably in the range from 1 to 6 bar. Working in a closed system at autogenic pressure can be especially preferred.

The duration of the hydrolytic cleavage usually lies in the range of a few hours, preferred is a treatment of 2 to 10 hours. The reaction mixture should be agitated during this time. When a closed reactor is used, agitator or shaker autoclaves can be utilized.

The process product frequently is obtained in the form of an emulsion from which the excess water can hardly be separated by decantation. A removal of the excess water from the reaction product can, however, be achieved by simple distillation under vacuum. The catalyst remains in the reaction product in this manner. These small amounts of catalyst do not interfere in many applications. If desired, the catalyst can be separated in a conventional manner.

1,2-diols are used extensively. They can be used in creams and skin care products and are known as especially good for the skin since they are found in lanolin. They, as well as their boric acid derivatives, are recommended as textile softeners and, in the form of their carboxylic acid derivatives, as foam regulators in detergents and cleaning agents.

The ethoxylates of 1,2-diols are excellent nonionic tensides with very good washing properties. They have a similarly wide range of application as do the fatty alcohol ethoxylates.

1,2-alkanediols with chain lengths in the range from 10 to 20 carbon atoms, and here particularly the range from 12 to 16 carbon atoms, can be especially important for technical applications. According to the invention, the preparation of diols of this type, for example, a technical 12/14-diol mixture, at temperatures of up to about 135° C. and pressures not exceeding 3 bar becomes possible with high yields.

The following examples illustrate the practice of the invention without being limitative in any respect.

EXAMPLES

Examples 1 to 30

The results of the process according to the invention are summarized, grouped according to variations, in the following Examples 1 to 30. No attempt was made to improve the process conditions with respect to a high yield in each individual case, since these examples are designed to show the scope of the invention.

The first group of Examples 1 to 8 was concerned with the use of various amines. Technical grade distilled dodecene oxide and, as second catalyst component, acetic acid were used in this test series. The reaction conditions for this test group were 160° C., 7 bar and four hours of reaction.

The second test group (Examples 9 to 12) describes the reaction of epoxides of different chain lengths. N,N-dimethyl-2-hydroxydodecylamine/acetic acid was used as catalyst in a mol ratio of 1: about 1.2. The catalyst system was employed in an amount of about 5 mol % (amine+acid), based on the epoxide. The reaction conditions were 160° C., 7 bar and 6 hours of treatment.

The third test group (Examples 13-18) is concerned with the use of various acids as second catalyst component. Technical grade, distilled dodecene oxide was used as starting material, trimethylamine was used as amine component. The mol ratio of amine to acid was 1:1.27 and the catalyst system was employed in an amount about 5 mol % (amine+acid), based on the epoxide. The reaction conditions were 120° C., 3 bar and 4 hours reaction time in these cases.

In the fourth group (Examples 19-27), combinations of amines with longer chains and carboxylic acids with longer chains were used. The epoxide used as starting material was dodecene oxide. Again the ratios of the amine to acid were 1: about 1.2 and the catalyst system was employed in an amount of about 5 mol %. The reaction conditions were 100° C. and normal pressure with a reaction time of four hours. High yields were obtained even under these mild reaction conditions, and they are practically all above 40% and reach up to 60%. The high yields of desired end product needed in practice can be obtained by making the reaction conditions slightly more severe (longer reaction time and/or increase in temperature and pressure).

The last group (Examples 28-30) is concerned with the testing of quaternary ammonium salts at 160° C., 7 bar and four hours of reaction time with dodecene oxide as starting material.

The tests of Examples 1-30 were performed in the following manner. The olefin oxide was filled into an agitator autoclave together with water and the catalyst, and heated to the stipulated temperature for the given time. Thereafter, the reaction mixture was transferred from the autoclave to a conventional vacuum distillation setup and the water was evaporated under water jet vacuum (about 12 torr) until a pot temperature of 110° C. was reached. This was followed by distillation under oil pump vacuum at about 2 mbar, with a separation into a pre-run, a main fraction, a last fraction and the pot residue. The pre-run was analyzed for the epoxide (EpO) value, the main fraction for the EpO and the hydroxyl (OH) number. The small amounts of catalyst were not separated but left in the substance, therefore the values of the fractions were more than 100%. The results are compiled in Table 1.

TABLE 1

| Example | Epoxide Type | Purity | % EpO | Catalyst Amine component Type | Amount gm | Acid component Type | Amount gm | Final Products Pre-Run % | % EpO | Main fraction % | % EpO | OH-# | Last run % | Residue % |
|---|---|---|---|---|---|---|---|---|---|---|---|---|---|---|
| 1 | 1 mol tech. α C12 dist. | | 8.23 | 4-(dimethyl-amino)-pyridine | 5 | Acetic Acid | 3.1 | 3.2 | 0.40 | 90.2 | 0.02 | 537 | 3.9 | 8.1 |
| 2 | 1 mol tech. α C12 dist. | | " | triethylene-diamine (diaza-bicyclo-octane) | 5 | Acetic Acid | 3.4 | 3.4 | 0.72 | 84.6 | 0.05 | 524 | 4.0 | 11.4 |
| 3 | 1 mol tech. α C12 dist. | | " | dimethyldo-decylamine | 5 | Acetic Acid | 1.78 | 2.91 | 0.34 | 94.6 | 0.034 | 527 | 6.0 | 1.7 |
| 4 | 1 mol tech. α C12 dist. | | " | trioctylamine | 5 | Acetic Acid | 1.06 | 81.5 | 8.17 | 13.7 | 0.32 | 419 | 0.2 | 1.0 |
| 5 | 1 mol tech. α C12 dist. | | " | methylamine, 40% solution | 1.63 | Acetic Acid | 1.60 | 67.4 | 7.7 | 23.4 | 0.20 | 503 | 5.1 | 1.1 |
| 6 | 1 mol tech. α C12 dist. | | " | dimethylamine, 40% solution | 2.42 | Acetic Acid | 1.60 | 5.0 | 0.87 | 89.5 | 0.058 | 534 | 5.7 | 1.9 |
| 7 | 1 mol tech. α C12 dist. | | " | trimethylamine, 45% solution | 2.76 | Acetic Acid | 1.60 | 3.4 | 0.67 | 91.5 | 0.085 | 541 | 5.9 | 0.9 |
| 8 | 1 mol tech. α C12 dist. | | " | dimethyl-(2-hydroxydodecyl)-amine | 5.0 | Acetic Acid | 1.60 | 3.5 | 0.40 | 92.1 | 0.04 | 539 | 6.2 | 1.2 |
| 9 | 3 mol dist. α-C8 | | 12.20 | dimethyl-(2-hydroxydode-cyl)-amine | 15.0 | acetic acid | 4.8 | 1.8 | 6.52 | 81.1 | 0.014 | 730 | 10.5 | 4.4 |
| 10 | 2 mol tech. α-C14 dist. | | 7.10 | dimethyl-(2-hydroxydode-cyl)-amine | 10 | acetic acid | 3.2 | 5.2 | 2.0 | 91.3 | 0.0 | 479 | 0.0 | 8.3 |
| 11 | 2 mol tech. α-C16 undist. | | 6.30 | dimethyl-(2-hydroxydode-cyl)-amine | 10 | acetic acid | 3.2 | 7.3 | 1.14 | 90.5 | 0.08 | 412 | 0.0 | 7.9 |
| 12 | 2 mol tech. α-C18 undist. | | 5.49 | dimethyl-(2-hydroxydode-cyl)-amine | 10 | acetic acid | 3.2 | 12.2 | 1.17 | 87.0 | 0.10 | 369 | 0.0 | 9.5 |
| 13 | 1 mol tech. α-C12 dist. | | 8.23 | trimethylamine, 45% solution | 2.76 | adipic acid | 1.94 | 64.5 | 8.03 | 18.6 | 0.48 | 528 | 7.31 | 6.32 |
| 14 | 1 mol tech. α-C12 dist. | | " | trimethylamine, 45% solution | " | lauric acid | 5.33 | 5.73 | 2.95 | 82.2 | 0.16 | 540 | 9.6 | 4.5 |
| 15 | 1 mol tech. α-C12 dist. | | " | trimethylamine, 45% solution | " | stearic acid | 7.56 | 5.04 | 2.83 | 86.4 | 0.13 | 528 | 7.07 | 8.55 |
| 16 | 1 mol tech. α-C12 dist. | | " | trimethylamine, 45% solution | " | tech. oleic acid | 7.40 | 4.84 | 2.90 | 83.5 | 0.19 | 5.29 | 11.4 | 5.9 |
| 17 | 1 mol tech. α-C12 dist. | | " | trimethylamine, 45% solution | " | tech. erucic acid | 9.03 | 5.1 | 2.95 | 83.4 | 0.006 | 534 | 8.75 | 9.0 |
| 18 | 1 mol tech. α-C12 dist. | | " | trimethylamine, 45% solution | " | 85% H3PO4 | 1.3 | 47.0 | 7.5 | 20.2 | 0.32 | 530 | 3.6 | 20.6 |
| 19 | 1 mol tech. α-C12 dist. | | 8.23 | dimethyl-2-hydroxyoctyl-amine | 3.60 | capryl-ic acid | 3.80 | 37.9 | 7.5 | 46.3 | 0.06 | 527 | 15.4 | 2.8 |
| 20 | 1 mol tech. α-C12 dist. | | " | dimethyl-2-hydroxydodecyl-amine | 5.12 | lauric acid | 5.33 | 34.5 | 7.54 | 49.4 | 0.18 | 532 | 15.3 | 4.1 |
| 21 | 1 mol tech. α-C12 dist. | | " | dimethyl-2-hydroxy-C16/18-alkylamine | 6.73 | stearic acid | 7.56 | 45.9 | 7.68 | 36.8 | 0.38 | 520 | 11.8 | 11.0 |
| 22 | 1 mol tech. α-C12 dist. | | " | dimethyl-2-hydroxy-C16/18-alkylamine | " | erucic acid | 9.03 | 43.5 | 7.72 | 42.1 | 0.35 | 512 | 7.4 | 11.9 |
| 23 | 1 mol tech. α-C12 dist. | | " | dimethyl-2-hydroxydode-cylamine | 5.12 | erucic acid | " | 34.0 | 7.51 | 48.7 | 0.80 | 534 | 10.3 | 12.1 |
| 24 | 1 mol tech. α-C12 dist. | | " | dimethyl-2-hydroxydode-cylamine | " | stearic acid | 7.65 | 32.9 | 7.57 | 48.5 | 0.10 | 534 | 18.2 | 5.1 |
| 25 | 1 mol tech. α-C12 dist. | | " | dimethyldode-cylamine | 5.0 acid | stearic acid | 7.56 | 24.7 | 6.66 | 61.7 | 0.05 | 532 | 11.0 | 8.3 |
| 26 | 1 mol tech. α-C12 dist. | | " | dimethyl-2-hydroxydodecyl-amine | 5.12 | azelaic acid | 5.10 | 42.8 | 8.10 | 42.3 | 0.19 | 532 | 5.6 | 12.0 |
| 27 | 1 mol tech. α-C12 dist. | | " | dimethyl-2-hydroxydodecyl-amine | 5.12 acid | sebacic acid | 5.38 | 39.6 | 7.70 | 45.2 | 0.13 | 538 | 6.9 | 11.8 |
| 28 | 1 mol tech. αC12 dist | | 8.23 | methyltri-octylammon-ium chloride | 5.0 | acetic acid | 0.94 | 8.0 | 3.62 | 84.5 | 0.17 | 527 | 10.8 | 1.2 |
| 29 | 1 mol tech. | | " | dimethyl- | 5.0 | acetic | 0.17 | 4.6 | 1.76 | 88.8 | 0.06 | 541 | 9.5 | 1.1 |

TABLE 1-continued

| Example | Epoxide Type | Purity | % EpO | Catalyst Amine component Type | Amount gm | Acid component Type | Amount gm | Final Products Pre-Run % | % EpO | Main fraction % | % EpO | OH-# | Last run % | Residue % |
|---|---|---|---|---|---|---|---|---|---|---|---|---|---|---|
|  | αC12 dist |  |  | bis-(2-hydroxy-dodecyl)-ammonium acetate |  | acid |  |  |  |  |  |  |  |  |
| 30 | 1 mol tech. αC12 dist |  | " | dimethyl-distearyl-ammonium chloride, 75% | 5.0 | — | 0.0 | 26.7 | 6.73 | 60.0 | 0.22 | 542 | 12.8 | 2.5 |

EXAMPLE 31

One mol of hexene-1 oxide (EpO 15.4%, molar weight calculated from this: 103.9) was transferred with 1.6 gm of acetic acid, 2.42 gm of a 40% aqueous dimethylamine solution and 50 gm of water into an agitator autoclave and maintained at 120° C. for 4 hours, during which a pressure of 7.8 bar was reached. The distillation yielded 2.6% pre-run, 87.4% 1,2-hexanediol and 1.2% of the theoretical residue. the percentages are based on the molar weight of 1,2-hexanediol (118.2).

EXAMPLE 32

One mol of cetylglycidyl ether (EpO 4.38%, molar weight calculated from this: 365.3) was transferred together with 50 gm of water, 2.42 gm of a 40% aqueous dimethylamine solution and 1.6 gm of acetic acid, and heated to 135° C. for 6 hours. The final product was dried under vacuum. The hydroxyl number was determined as 284. The yield is at least 80%.

EXAMPLE 33

One-half mol of bisphenol-A diglycidyl ether (EpO 8.61%, molar weight calculated from it: 371.8) together with 50 gm of water, 2.42 gm of a 40% dimethylamine solution in water and 1.6 gm of acetic acid were heated to 135° C. for 6 hours in the agitator autoclave. The final product dried under vacuum had the analytical data OH-number 495, EpO 0.14%; yield at least 80%.

EXAMPLE 34

One mol styrene oxide (EpO 12.53%, molar weight calculated from this: 127.6) and 50 gm of water, 2.42 gm of a 40% dimethylamine solution in water and 1.6 gm of acetic acid were kept at 135° C. for 6 hours in the agitator autoclave. Obtained by distillation were 110.9 gm (80.2% theor.) of phenyl ethylene glycol (OH-number 773; EpO 0.0%).

EXAMPLE 35

One mol of dodecene oxide and 50 gm of water, 4.84 gm of a 40% aqueous dimethylamine solution and 10.7 gm of lauric acid were refluxed for 8 hours. The water was then removed under water jet vacuum and the remaining substance was distilled under oil pump vacuum. Obtained were 177.2 gm of dodecanediol, Bp 114°–165° C. at 0.1 mbar; OH-number 506 (calc. 555), Amine number 8.74; acid number 0.27 (yield 87.6% of theory).

EXAMPLE 36

One mol of hexene oxide and 50 gm of water, 2.42 gm of a 40% aqueous dimethylamine solution and 1.6 gm of acetic acid were placed in an autoclave and heated to 120° C. for 4 hours. After distilling off the water under water jet vacuum, the final product was also distilled under 12 torr water jet vacuum. Obtained were 103 gm (87% of theory of hexanediol. $Bp_{12}$ 114°–145° C.; OH-number 901 (calc. 949).

EXAMPLE 37

One mol of dodecene oxide, 50 gm of water, 2.42 gm of a 40% aqueous dimethylamine solution and 4.1 gm of citric acid were kept at 160° C. for 4 hours, under autogenic pressure. Obtained were 183.1 gm (90.5% of theory) of diol. When benzoic acid was used instead of the citric acid, the desired diol was obtained with a yield of 68.6% of the theory, after 4 hours at 120° C.

The use of p-aminobenzoic acid led to a diol yield of 46.2% of the theory, in the same experiment after 4 hours at 120° C. With reaction conditions changed to 6 hours at 160° C., the diol was produced with a yield of 81% of the theory.

All percentages appearing in the specification refer to percent by weight, if not otherwise indicated.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. In the process for the production of 1,2-diols having at least 4 carbon atoms comprising subjecting a 1,2-epoxide having at least 4 carbon atoms to hydrolysis with water in the presence of a catalyst at elevated temperatures and recovering 1,2-diols having at least 4 carbon atoms, the improvement consisting of employing from 0.5 to 10 mol %, based on the epoxide employed of a catalyst system selected from the group consisting of:

(1) salts of amines selected from the group consisting of monoalkyl amines having from 1 to 18 carbon atoms, dialkylamines having from 1 to 18 carbon atoms in each alkyl, trialkylamines having from 1 to 18 carbon atoms in each alkyl, alkylol-dialkylamines having from 1 to 18 carbon atoms in each alkyl and alkylol, phenylalkylamines having from 1 to 8 carbon atoms in the alkyl, cyclodiazaalkanes having from 4 to 8 carbon atoms, and pyridinyl-dialkylamine having from 1 to 8 carbon atoms in the alkyl with acids selected from the group consisting of:

(a) an organic acid selected from the group consisting of alkanoic acids having from 1 to 26 carbon atoms, alkanedioic acids having from 2 to 26 carbon atoms, alkanetrioic acids and hydroxyalkanetrioic acids having from 4 to 26 carbon atoms, hydroxyalkanoic acids having from 2 to 26 carbon atoms, chloroalkanoic acids having from 2 to 26 carbon atoms, dichloroalkanoic acids having from 2 to 26 carbon atoms, trichloroalkanoic acids having from 2 to 26 carbon atoms, benzoic acid, phenyl alkanoic acids having from 8 to 24 carbon atoms, phenylalkenoic acids having from 9 to 24 carbon atoms, benzene dicarboxylic acids, pyromucic acid, and tetrahydrofuran carboxylic acids, and (b) strong mineral acids, (2) quaternary ammonium salts selected from the group consisting of tetraalkyl ammonium salts and phenylalkyl trialkyl ammonium salts with the above acids, and (3) mixtures thereof, wherein the molar ratio of amine or ammonium to acid is from 1:1.1 to 1.8, as said catalyst.

2. The process of claim 1 wherein the molar ratio of amine or ammonium to acid is from 1:1.1 to 1.5.

3. The process of claim 1 or 2 wherein an amine is employed having a number of carbon atoms according to the number of carbon atoms of said 1,2-epoxide having at least 4 carbon atoms in the following amounts:

(1) the amine is a mono-alkylamine and the sum of the carbon atoms therein + three times the sum of the carbon atoms in the alkene-1 oxide is from 13 to 40.

(2) the amine is a dialkylamine and the sum of the carbon atoms therein + two times the sum of the carbon atoms in the alkene-1 oxide is from 10 to 40, (3) the amine is a trialkylamine and the sum of the carbon atoms therein + the sum of the carbon atoms in the alkene-1 oxide is from 7 to 40.

4. The process of claim 3 wherein the range of the sum of the carbon atoms in amine and alkene-1 oxide is from 12 to 30.

5. The process of claim 3 wherein said amine is a dialkylamine having from 2 to 8 carbon atoms.

6. The process of claim 5 wherein said dialkylamine has from 2 to 4 carbon atoms.

7. The process of claim 6 wherein said dialkylamine is a salt of dimethylamine.

8. The process of claim 1 or 2 wherein said amount of said catalyst system is from 1 to 6 mol %.

9. The process of claim 1 or 2 wherein said 1,2-epoxide has the formula

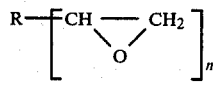

wherein R is a member having from 2 to 28 carbon atoms selected from the group consisting of alkyl, alkenyl, alkadienyl, cycloalkyl, cycloalkenyl, phenyl, naphthyl, alkoxyalkyl, alkenyloxyalkyl, alkadienyloxyalkyl, cycloalkyloxyalkyl, cycloalkenyloxyalkyl, phenyloxyalkyl, naphthyloxyalkyl and bisphenol-A-dioxyalkyl, and n is an integer from 1 to 5.

10. The process of claim 9 wherein R is alkyl having from 8 to 12 carbon atoms and n is 1.

11. In the process for the preparation of higher 1,2-diols and/or higher 1,2-polyols which comprises hydrolyzing the corresponding epoxides of the formula:

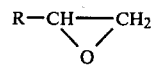

in which R is selected from the group consisting of alkyl having 2 to 28 carbon atoms, haloalkyl having 2 to 28 carbon atoms, alkoxyalkyl having 2 to 28 carbon atoms, epoxyalkyl having 3 to 28 carbon atoms, haloepoxyalkyl having 3 to 28 carbon atoms, alkoxyepoxyalkyl having from 4 to 28 carbon atoms, and mixtures thereof, with the proviso that the total number of carbon atoms in the epoxide is from 4 to 30 carbon atoms, with a solution of a catalyst, and recovering said diols and/or polyols; the improvement consisting of employing from 0.5 to 10 mol % based on the epoxide employed of a catalyst system selected from the group consisting of:

(1) salts of amines selected from the group consisting of monoalkyl amines having from 1 to 18 carbon atoms, dialkylamines having from 1 to 18 carbon atoms in each alkyl, trialkylamines having from 1 to 18 carbon atoms in each alkyl, alkylol-dialkylamines having from 1 to 18 carbon atoms in each alkyl and alkylol, phenylalkylamines having from 1 to 8 carbon atoms in the alkyl, cyclodiazaalkanes having from 4 to 8 carbon atoms, and pyridinyldialkylamine having from 1 to 8 carbon atoms in the alkyl with acids selected from the group consisting of:

(a) an organic acid selected from the group consisting of alkanoic acids having from 1 to 26 carbon atoms, alkanedioic acids having from 2 to 26 carbon atoms, alkanetrioic acids and hydroxyalkanetrioic acids having from 4 to 26 carbon atoms, hydroxyalkanoic acids having from 2 to 26 carbon atoms, chloroalkanoic acids having from 2 to 26 carbon atoms, dichloroalkanoic acids having from 2 to 26 carbon atoms, trichloroalkanoic acids having from 2 to 26 carbon atoms, benzoic acid, phenyl alkanoic acids having from 8 to 24 carbon atoms, phenylalkenoic acids having from 9 to 24 carbon atoms, benzene dicarboxylic acids, pyromucic acid, and tetrahydrofuran carboxylic acids, and (b) strong mineral acids, (2) quaternary ammonium salts selected from the group consisting of tetraalkyl ammonium salts and phenylalkyl trialkyl ammonium salts with the above acids, and (3) mixtures thereof, wherein the molar ratio of amine or ammonium to acid is from 1:1.1 to 1.8, as said catalyst.

12. The process of claim 11 wherein said process is conducted at temperatures of from 100° to 180° C., and pressures of from 1 to 10 bars, in the presence of 1 to 10 mols of water per mol of epoxide, for 2 to 10 hours.

* * * * *